(12) United States Patent
Lin et al.

(10) Patent No.: US 11,517,597 B2
(45) Date of Patent: *Dec. 6, 2022

(54) METHOD FOR IMPROVING SKIN CONDITION WITH POSTBIOTIC EXTRACT

(71) Applicant: CHAMBIO CO., LTD., Taichung (TW)

(72) Inventors: Meei-Yn Lin, Taichung (TW);
Hung-Pin Chiu, Taichung (TW);
Yi-Heng Chiu, Taichung (TW)

(73) Assignee: CHAMBIO CO., LTD., Taichung (TW)

( * ) Notice: Subject to any disclaimer, the term of this patent is extended or adjusted under 35 U.S.C. 154(b) by 0 days.

This patent is subject to a terminal disclaimer.

(21) Appl. No.: 17/037,195

(22) Filed: Sep. 29, 2020

(65) Prior Publication Data

US 2022/0096573 A1    Mar. 31, 2022

(51) Int. Cl.
| | |
|---|---|
| *A61K 35/747* | (2015.01) |
| *A61K 35/745* | (2015.01) |
| *A61K 35/00* | (2006.01) |
| *A61K 47/42* | (2017.01) |
| *A61K 8/99* | (2017.01) |
| *A61P 17/02* | (2006.01) |
| *A61Q 19/08* | (2006.01) |
| *A61K 47/36* | (2006.01) |

(52) U.S. Cl.
CPC .............. *A61K 35/747* (2013.01); *A61K 8/99* (2013.01); *A61K 35/745* (2013.01); *A61K 47/36* (2013.01); *A61K 47/42* (2013.01); *A61P 17/02* (2018.01); *A61Q 19/08* (2013.01); *A61K 2035/115* (2013.01)

(58) Field of Classification Search
None
See application file for complete search history.

(56) References Cited

U.S. PATENT DOCUMENTS

| | | | | |
|---|---|---|---|---|
| 10,022,409 | B2 * | 7/2018 | Carpenter | A61P 17/00 |
| 11,040,077 | B2 * | 6/2021 | Brucker | A61P 17/00 |
| 11,096,874 | B2 * | 8/2021 | Rajaiah | A61K 8/22 |
| 2019/0192590 | A1 * | 6/2019 | Biffi | A23L 33/16 |
| 2020/0345799 | A1 * | 11/2020 | Brucker | A61P 31/04 |
| 2021/0128452 | A1 * | 5/2021 | Dhir | A61K 8/64 |
| 2021/0236566 | A1 * | 8/2021 | Biffi | A61Q 19/001 |
| 2021/0386802 | A1 * | 12/2021 | Brucker | A61K 31/404 |
| 2022/0096571 | A1 * | 3/2022 | Lin | A23L 33/17 |
| 2022/0096573 | A1 * | 3/2022 | Lin | A61K 47/42 |

FOREIGN PATENT DOCUMENTS

| | | | | |
|---|---|---|---|---|
| EP | 3856131 A1 * | 8/2021 | | A61Q 19/00 |
| WO | WO-2020064977 A1 * | 4/2020 | | A61Q 19/00 |
| WO | WO-2020210553 A1 * | 10/2020 | | A61K 31/404 |
| WO | WO-2021093632 A1 * | 5/2021 | | |
| WO | WO-2021110768 A1 * | 6/2021 | | A61Q 5/02 |

OTHER PUBLICATIONS

Majeed et al, Cosmetics. 2020, 776, 14 pages. Published: Sep. 27, 2020 (Year: 2020).*

Prajapti et al, International Journal of Research in Ayurveda and Pharmacy. May 2021. 12/3:99-102. abstract only. (Year: 2021).*

Hernández-Rodríguez, L., et al., "Lactobacillus plantarum protection by entrapment in whey protein isolate: k-carrageenan complex coacervates," Food Hydrocolloids, 2014, 36:181-188.

Nam, B., et al., "Regulatory effects of Lactobacillus plantarum HY7714 on skin health by improving intestinal condition," Plos One, 2020, 15(4):e0231268 (14 pages).

Search Report appended to an Office Action, which was issued to Taiwanese counterpart application No. 109115725 by the TIPO dated Jul. 6, 2021, with an English translation thereof.

* cited by examiner

*Primary Examiner* — S. Devi

(74) *Attorney, Agent, or Firm* — Mh2 Technology Law Group, LLP

(57) ABSTRACT

A method for improving skin condition includes administering to a subject in need thereof a postbiotic extract. The postbiotic extract is prepared by a process including the steps of providing a first material having a first isoelectric point ranging from pH 1 to pH 6 and a second material having a second isoelectric point ranging from pH 4 to pH 8, admixing the first material and a probiotic microorganism with water having a pH greater than the second isoelectric point, so as to form a mixture, adding the second material into the mixture and then adjusting a pH of the second material-added mixture to between the first and second isoelectric points so that a precipitate is formed, and subjecting the precipitate to a cell wall isolation treatment to obtain the postbiotic extract.

2 Claims, 1 Drawing Sheet

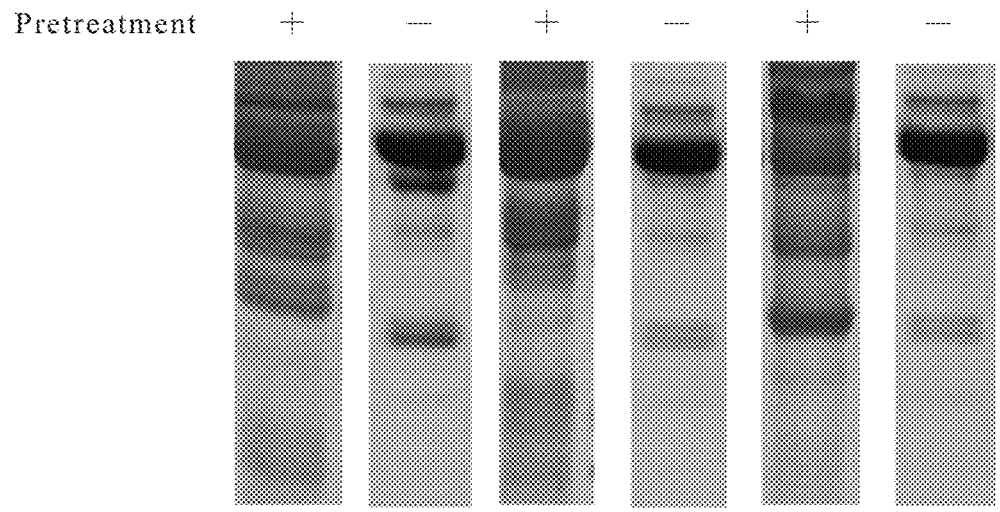
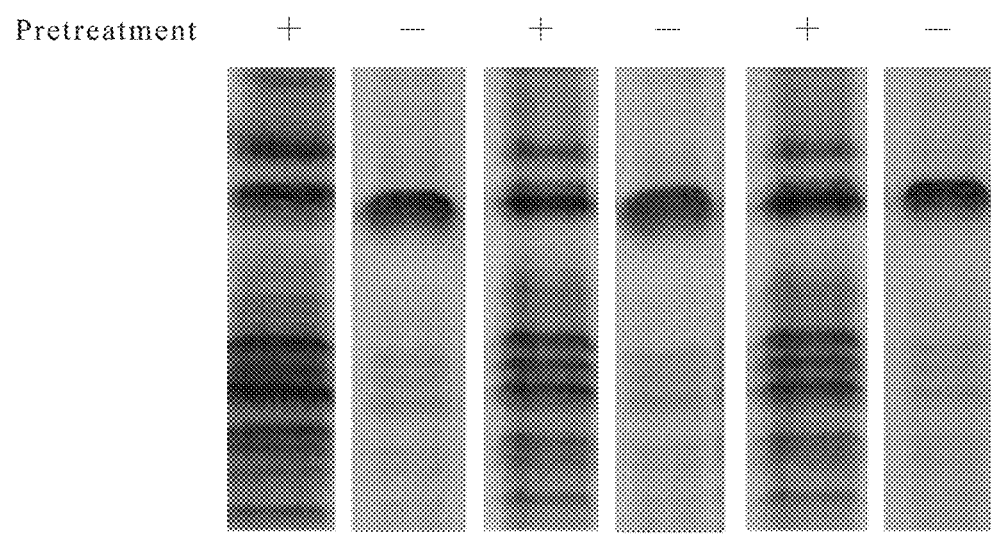

METHOD FOR IMPROVING SKIN CONDITION WITH POSTBIOTIC EXTRACT

FIELD

The present disclosure relates to a method for improving skin condition with a postbiotic extract.

BACKGROUND

Probiotics are resident normal flora of the intestinal tract and believed to play important roles in regulating proper intestinal immunity and digestion by balancing intestinal microflora. These beneficial microorganisms are widely used as live microbial dietary supplement and can help restoring intestinal microfloral balance. Many species of lactic acid bacteria (LAB), such as *Lactobacillus* spp., *Lactococcus* spp., *Streptococcus* spp., *Enterococcus* spp., and *Bifidobacterium* spp., are generally considered as probiotics. Furthermore, some of *Bacillus* spp. and some yeasts and *Saccharomyces* spp. have also been found as suitable candidates.

Probiotics are viable by definition, and their stability and viability are considered to be crucial for their health benefits. Paraprobiotics or postbiotics have emerged to denote that non-viable microbial cells, microbial fractions, or cell lysates might also offer physiological benefits to the host by providing additional bioactivity. Postbiotic efficacy is based on the microbial metabolites, proteins, lipids, carbohydrates, vitamins, organic acids, cell wall components, or other complex molecules that are generated in the matrix that is fermented. These postbiotics have drawn attention because of their clear chemical structure, safety dose parameters, long shelf life and the content of various signaling molecules which may have anti-inflammatory, immunomodulatory, anti-obesogenic, antihypertensive, hypocholesterolemic, anti-proliferative, and antioxidant activities.

Skin is the largest organ of the body and functions primarily to protect the body from external factors (such as microorganisms, chemicals, UV radiation, and temperature). Skin aging is a complex biological process affecting various layers of the skin and the hypodermis and can be divided into intrinsic aging and extrinsic aging. Intrinsic aging induces a progressive loss of extracellular matrix (ECM), cellularity, and elasticity of skin with age. Extrinsic aging (also known as photo-aging) refers to a declination process caused by environmental factors, which include smoking, chemical exposure, and primarily ultraviolet-B (UV-B) exposure. Extrinsic aging is characterized by fine and coarse wrinkling, roughness, dryness, laxity, and pigmentary lesion. In the dermis, UV-B exposure has been shown to stimulate collagenase production by human dermal fibroblasts (HDF) and to up-regulate collagenase gene expression. This induces degeneration of collagen and deposition of altered elastic tissue which is prominent as wrinkles and yellow discoloration of skin.

Growth factors are typically peptides with diverse biological effects. Some growth factor families that have been identified as useful in wound healing, angiogenesis, and epidermal remodeling include, e.g., transforming growth factor-β (TGF-β), epidermal growth factor (EGF), insulin-like growth factors (IGFs), platelet-derived growth factor (PDGF), and fibroblast growth factors (FGFs). The growth factors that stimulate collagen production in wound healing might provide benefits for aging skin. Accordingly, such growth factors are being incorporated into anti-aging cosmeceuticals.

TGF-β is considered to be a multifunctional cytokine, and plays a regulatory role in cellular growth, differentiation, immunity and inflammatory responses, and extracellular matrix protein synthesis. It has been reported that fibroblast to myofibroblast differentiation drives effective wound healing and is largely regulated by TGF-β.

Skin regeneration has become the focus of cosmeceuticals and dermatologists treating an aging population. Various noninvasive treatments and topical cosmeceuticals have been used to treat some symptoms of skin aging. However, none of these methods can individually completely eliminate wrinkles or enhance the repair of damaged skin, and hence multiple and often expensive treatments are required.

In view of the foregoing, the applicant attempted to develop a more efficient and economical method for improving skin condition.

SUMMARY

Therefore, an object of the disclosure is to provide a method for improving skin condition that can alleviate at least one of the drawbacks of the prior art.

The method includes administering to a subject in need thereof a postbiotic extract, which is prepared by a process including the steps of:
a) providing a first material having a first isoelectric point ranging from pH 1 to pH 6, and a second material having a second isoelectric point ranging from pH 4 to pH 8, wherein the second isoelectric point is greater than the first isoelectric point, and the first isoelectric point and the second isoelectric point have a pH difference ranging from 0.5 and 3;
b) admixing the first material and a probiotic microorganism with water having a pH value greater than the second isoelectric point, so as to form a mixture;
c) adding the second material into the mixture, followed by adjusting a pH value of the second material-added mixture to between the first isoelectric point and the second isoelectric point, so that a precipitate is formed; and
d) subjecting the precipitate to a cell wall extraction treatment to obtain the postbiotic extract.

BRIEF DESCRIPTION OF THE DRAWINGS

The above and other objects, features and advantages of the present disclosure will become apparent with reference to the following detailed description and the exemplary embodiments taken in conjunction with the accompanying drawings, in which:

FIG. 1 is a digital image showing a result of sodium dodecyl sulfate-polyacrylamide gel electrophoresis (SDS-PAGE) analysis of postbiotic extracts of Example 1, infra.

DETAILED DESCRIPTION

It is to be understood that, if any prior art publication is referred to herein, such reference does not constitute an admission that the publication forms a part of the common general knowledge in the art, in Taiwan or any other country.

For the purpose of this specification, it will be clearly understood that the word "comprising" means "including but not limited to", and that the word "comprises" has a corresponding meaning.

Unless defined otherwise, all technical and scientific terms used herein have the meaning commonly understood by a person skilled in the art to which the present disclosure belongs. One skilled in the art will recognize many methods and materials similar or equivalent to those described herein, which could be used in the practice of the present disclosure. Indeed, the present disclosure is in no way limited to the methods and materials described.

As used herein, the term "skin condition" refers to skin regeneration, skin elasticity, skin wrinkles, skin aging, and wound healing.

The present disclosure provides a method for improving skin condition, including administering to a subject in need thereof a postbiotic extract. Such postbiotic extract is prepared by a process including the steps of:

a) providing a first material having a first isoelectric point ranging from pH 1 to pH 6, and a second material having a second isoelectric point ranging from pH 4 to pH 8, wherein the second isoelectric point is greater than the first isoelectric point, and the first isoelectric point and the second isoelectric point have a pH difference ranging from 0.5 and 3;

b) admixing the first material and a probiotic microorganism with water having a pH value greater than the second isoelectric point, so as to form a mixture;

c) adding the second material into the mixture, followed by adjusting a pH value of the second material-added mixture to between the first isoelectric point and the second isoelectric point, so that a precipitate is formed; and d) subjecting the precipitate to a cell wall extraction treatment to obtain the postbiotic extract.

According to the present disclosure, the probiotic microorganism may be selected from the group consisting of *Bacillus* spp., *Streptococcus* spp., *Lactococcus* spp., *Abiotrophia* spp., *Aerococcus* spp., *Carnobacterium* spp., *Enterococcus* spp., *Lactobacillus* spp., *Leuconostoc* spp., *Oenococcus* spp., *Pediococcus* spp., *Tetragenococcus* spp., *Vagococcus* spp., *Weissella* spp., *Bifidobacterium* spp., *Saccharomyces* spp., *Kluyveromyces* spp., *Staphylococcus* spp., *Pediococcus* spp., *Propionibacterium* spp., and combinations thereof.

According to the present disclosure, the *Lactobacillus* spp. may be selected from the group consisting of *Lactobacillus plantarum, Lactobacillus acidophilus, Lactobacillus casei, Lactobacillus rhamnosus, Lactobacillus paracasei*, and combinations thereof.

According to the present disclosure, the *Bifidobacterium* spp. may be selected from the group consisting of *Bifidobacterium bifidum, Bifidobacterium lactis, Bifidobacterium longum, Bifidobacterium breve, Bifidobacterium animalis*, and combinations thereof.

According to the present disclosure, the *Bacillus* spp. may be selected from the group consisting of *Bacillus coagulans, Bacillus subtilis, Bacillus clausii*, and combinations thereof.

According to the present disclosure, the probiotic microorganism may be alive or dead, concentrated or non-concentrated, or in the form of a liquid, a paste, a semi-solid, or a solid (e.g. a pellet, a granule, or a powder), and may be heat-inactivated, frozen, dried, or freeze-dried (for example, may be in a freeze-dried form or a spray/fluid bed dried form). In an exemplary embodiment, the probiotic microorganism is heat-inactivated and is in a spray-dried powder form.

According to the present disclosure, the heat inactivation of the probiotic microorganism may be conducted at 60° C. to 140° C. for 1 second to 30 minutes. In an exemplary embodiment, the heat inactivation is conducted at 73±2° C. for 15 seconds.

According to the present disclosure, the first material may be selected from the group consisting of nonfat dry milk, casein, whey proteins, soybean proteins, pea proteins, egg proteins, rice proteins, hydrolyzed proteins, corn proteins, wheat proteins, barley proteins, gelatin, collagen, amino acids (for instance, branched chain amino acids), chitosan, chitin, and combinations thereof. In an exemplary embodiment, the first material is a whey protein.

According to the present disclosure, the second material may be selected from the group consisting of sodium alginate, agar, carrageenan, pectin, arabic gum, xanthan gum, locust bean gum, starch (such as modified starch), trehalose, dextrin (such as resistant maltodextrin), syrup, guar gum, konjac powder, vegetable fiber, synthetic fiber, semi-synthetic fiber, and combinations thereof. In an exemplary embodiment, the second material is dextrin.

In an exemplary embodiment of the present disclosure, the first isoelectric point and the second isoelectric point have a pH difference of 0.8.

According to the present disclosure, the precipitate may be obtained by methods well known in the art, including but not limited to centrifugation, filtration, and gravity settling. In an exemplary embodiment, the precipitate is obtained by filtration.

As used herein, the terms "isolation treatment" and "extraction treatment" can be used interchangeably, and mean that a cell wall component or a microbial metabolite is to be separated from a cell wall, in which it was originally present, through a treatment.

According to the present disclosure, the procedures and conditions of the cell wall isolation treatment are within the expertise and routine skills of those skilled in the art (for example, see Pei-Jun Tian et al. (2015), *Int. J. Mol. Sci.*, 16(8): 20033-20049).

The present disclosure also provides a postbiotic extract which is prepared by a process as described above.

The present disclosure also provides a food product, which includes a postbiotic extract as described above.

According to the present disclosure, for preparing the food product, the postbiotic extract may be incorporated into an edible material using a standard technique well known to one of ordinary skill in the art. For instance, the aforesaid postbiotic extract may be directly added to the edible material, or may be utilized for preparing an intermediate composition (e.g., a food additive or a premix) suitable to be subsequently added to the edible material.

According to the present disclosure, the food product may be in the form of fermented foods, processed foods, health foods, or dietary supplements.

According to the present disclosure, the food product may further include an additional nutritional component for maintaining or improving skin health. The suitable nutritional component includes, but is not limited to, hyaluronic acid, sodium hyaluronate, vitamin C, glucosamine, chondroitin, type I collagen, type II collagen, type III collagen, fish skin collagen, fish scale collagen, undenatured type II collagen, porcine collagen, bovine collagen, sialic acid, anthocyanin, polyphenol, flavonoid, egg shell membrane, and the like.

According to the present disclosure, the food product may further include an additional food additive selected from the group consisting of starch, dextrin, lactose, maize flour, rice flour, tricalcium phosphate, silicon dioxide, magnesium stearate, calcium carbonate, glucose, sucrose, fructose, sugar alcohol, oligosaccharides, sugar substitutes, fruit juice powder, yeast powder, nonfat dry milk, casein, whey proteins, amino acids, citric acid, citrate, lactic acid, lactate, nucleotides, and their combinations.

In addition, the postbiotic extract according to the present invention may be prepared in the form of a pharmaceutical composition.

According to the present disclosure, the pharmaceutical composition may be formulated into a suitable dosage form for parenteral, oral or topical administration using technology well known to those skilled in the art. The suitable dosage form includes, but is not limited to, sterile powder, tablets, troches, lozenges, pellets, capsules, dispersible powder or granules, solutions, suspensions, emulsions, syrup, elixir, slurry, external preparations, and the like.

The pharmaceutical composition according to the present disclosure may further include a pharmaceutically acceptable carrier widely employed in the art of drug-manufacturing. For instance, the pharmaceutically acceptable carrier may include one or more of the following agents: solvents, buffers, emulsifiers, suspending agents, decomposers, disintegrating agents, dispersing agents, binding agents, excipients, stabilizing agents, chelating agents, diluents, gelling agents, preservatives, fillers, wetting agents, lubricants, absorption delaying agents, liposomes, and the like. The choice and amount of the aforesaid agents are within the expertise and routine skills of those skilled in the art.

According to the present disclosure, the postbiotic extract may be formulated into an external preparation suitable for topical application to the skin using technology well known to those skilled in the art. The external preparation includes, but is not limited to, emulsions, gels, ointments, creams, patches, liniments, powder, aerosols, sprays, lotions, serums, pastes, foams, drops, suspensions, salves, and bandages.

According to the present disclosure, the external preparation is prepared by admixing the pharmaceutical composition with a base that is well known and commonly used in the art.

According to the present disclosure, the base may include one or more of the following additives: water, alcohols, glycols, hydrocarbons (such as petroleum jelly and white petrolatum), waxes (such as paraffin and yellow wax), preserving agents, antioxidants, surfactants, absorption enhancers, stabilizing agents, gelling agents (such as Carbopol® 941, microcrystalline cellulose and carboxymethylcellulose), active agents, humectants, odor absorbers, fragrances, pH-adjusting agents, chelating agents, emulsifiers, occlusive agents, emollients, thickeners, solubilizing agents, penetration enhancers, anti-irritants, colorants, propellants, etc. The choice and amount of the aforesaid additives are within the expertise and the routine skills of those skilled in the art.

The dosage and the frequency of administration of the pharmaceutical composition according to the present disclosure may vary depending on the following factors: the severity of the disease to be treated, the route of administration, and the weight, age, physical condition and response of the subject to be treated. The daily dosage of the pharmaceutical composition according to the present disclosure may be administered in a single dose or in several doses.

The disclosure will be further described by way of the following examples. However, it should be understood that the following examples are solely intended for the purpose of illustration and should not be construed as limiting the disclosure in practice.

EXAMPLES

General Experimental Materials:
1. The probiotics used in the following experiments are listed in Table 1.

TABLE 1

| Bacteria | Strain | Source |
| --- | --- | --- |
| Lactobacillus spp. | Lactobacillus plantarum CB102 | Department of Food Science and Biotechnology, National Chung Hsing University, Taiwan |
| | Lactobacillus acidophilus JCM1132 | |
| | Lactobacillus casei JCM1134 | |
| Bifidobacterium spp. | Bifidobacterium bifidum JCM1255 | |
| | Bifidobacterium lactis JCM10602 | |
| | Bifidobacterium longum CB108 | |

2. Human foreskin fibroblast cell line Hs68 was purchased from the Bioresource Collection and Research Center of the Food Industry Research and Development Institute (BCRC of FIRDI, Taiwan). Hs68 cells were grown in a 10-cm Petri dish containing Dulbecco's Modified Eagle's Medium (DMEM) (Thermo Fisher Scientific) supplemented with 10% fetal bovine serum (FBS). The Hs68 cells were cultivated in an incubator with culture conditions set at 37° C. and 5% $CO_2$. Medium change was performed every two to three days. Cell passage was performed when the cultured cells reached 80%-90% of confluence.

3. The nutritional components for improving skin health used in the following experiments are listed in Table 2.

TABLE 2

| Nutritional component | Trade name | Source |
| --- | --- | --- |
| Sodium hyaluronate | Rooster comb extract | Chambio Co., Ltd. |
| Vitamin C | Vitamin C | |
| Glucosamine | Glucosamine | |
| Chondroitin | Chondroitin | |
| Type II collagen | BC Collagen II | |
| Fish skin and scale collagen peptide | ActivColla LMW1000 | |
| Undenatured type II collagen | Non-denatured type II collagen | |

General Procedures:
1. Determination of transforming growth factor-β (TGF-β) content The TGF-β content was determined using an enzyme-linked immunosorbent assay (ELISA) kit (Cat. No. 559119, BD Biosciences) in accordance with the manufacturer's instructions.

Example 1. Preparation of Postbiotic Extract of Present Disclosure

A respective one of *Lactobacillus plantarum* CB102 (deposited at the Deutsche Sammlung von Mikroorganismen und Zellkulturen (DSMZ) GmbH (Inhoffenstraße 7B, 38124 Braunschweig, Germany) on 6 Sep. 2021), *Lactoba-* cillus acidophilus JCM1132, *Lactobacillus casei* JCM1134, *Bifidobacterium bifidum* JCM1255, *Bifidobacterium lactis* JCM10602, and *Bifidobacterium longum* CB108 (deposited at the Deutsche Sammlung von Mikroorganismen und Zellkulturen (DSMZ) GmbH (Inhoffenstraße 7B, 38124 Braunschweig, Germany) on 6 Sep. 2021) was inoculated in a Lactobacilli MRS broth (BD DIFCO, Cat. No. DF0881-17-5), and was then cultivated in an incubator (37° C., 5% $CO_2$) for 16 hours. The respective resultant culture was inactivated by high-temperature short-time (HTST) pasteurization (73±2° C., 15 seconds), followed by centrifugation at 10,000 rpm and 25° C. for 15 minutes. The resultant cell pellet was collected, followed by spray-drying. A portion of the respective dried bacterial cell powder was subjected to a pretreatment as follows.

A suitable amount of whey protein having an isoelectric point of 4.4 (NZMP, Cat. No. WPC80) was dissolved in water, and the resultant 10% whey protein solution (w/v, g/L) was adjusted to pH 7.5 through addition of sodium carbonate, followed by adding a suitable amount of a respective one of the six dried bacterial cell powders obtained above under agitation to reach a final concentration of 5% (w/v, g/L). Thereafter, dextrin having an isoelectric point of 5.2 (ZHUCHENG DONGXIAO, Cat. No. Maltodextrin DE8-10) was slowly added into the resultant mixture to reach a final concentration of 6% (w/v, g/L), followed by adjusting the dextrin-added mixture to a pH of 4.8 using lactic acid, so that a precipitate was formed due to charge neutralization. Filtration was conducted using a filter paper having a pore size of 25 µm, so as to obtain the precipitate. The precipitate was subjected to a spray drying treatment, thereby obtaining a pretreated bacterial cell powder.

The isolation and extraction of the cell wall of each pretreated bacterial cell powder was conducted using a method slightly modified from that described by Pei-Jun Tian et al. (2015), Int. J. Mol. Sci., 16 (8): 20033-20049. Briefly, 50 mg of the respective pretreated bacterial cell powder was mixed with 1 mL of 10% lactic acid, followed by heating in a water bath incubator (80° C.) for 60 minutes. After centrifugation at 10,000 g for 15 minutes, the resultant pellet was collected and was mixed with 1 mL of a solution containing a 0.5 M citrate solution and ethanol (4:10, v/v, pH 4.6), followed by incubation overnight. After centrifugation at 10,000 g for 20 minutes, the pellet thus obtained was washed with 95% ethanol, followed by heating in a dry bath incubator (80° C.) for 40 minutes to remove ethanol. Thus, a postbiotic extract was obtained. Such postbiotic extract was used for the following example and is referred to as "the postbiotic extract of the present disclosure" hereinafter.

In addition, for the sake of comparison, another portion of the respective one of the six dried bacterial cell powders, which was not pretreated according to the procedures described above, was subjected to the same isolation and extraction processes. The postbiotic extract thus obtained was used for the following example and is referred to as "the postbiotic extract of the prior art" hereinafter.

Example 2. Analysis of Extraction Yield and Protein Content

In order to determine the extraction yield and the protein content, the postbiotic extract of the present disclosure and the postbiotic extract of the prior art obtained in Example 1 were subjected to the following analyses.

A. Determination of Extraction Yield

The weight of each of the twelve postbiotic extracts was recorded. The extraction yield (%) of the respective postbiotic extract was calculated using the following Equation (I):

$$A=(B/50)\times 100 \qquad (I)$$

where A=extraction yield (%)

B=weight of respective postbiotic extract (mg)

The result is shown in Table 3 below. It can be seen from Table 3 that the extraction yields of the six postbiotic extracts of the present disclosure were significantly higher than those of the six postbiotic extracts of the prior art, indicating that the process of the present disclosure can effectively produce postbiotic extracts from probiotics.

TABLE 3

| | Extraction yield (%) | |
|---|---|---|
| Strain | The postbiotic extract of the present disclosure | The postbiotic extract of the prior art |
| *Lactobacillus plantarum* CB102 | 43.34% | 21.40% |
| *Lactobacillus acidophilus* JCM1132 | 44.14% | 20.54% |
| *Lactobacillus casei* JCM1134 | 43.94% | 21.11% |
| *Bifidobacterium bifidum* JCM1255 | 30.97% | 15.44% |
| *Bifidobacterium lactis* JCM10602 | 31.24% | 15.83% |
| *Bifidobacterium longum* CB108 | 31.82% | 16.75% |

B. Determination of Protein Content

The respective postbiotic extract was dissolved in a phosphate buffer solution (containing 8 g/L NaCl, 0.2 g/L KCl, 1.44 g/L $Na_2HPO_4$, and 0.24 g/L $KH_2PO_4$, and having a pH of 6.2), followed by determining the protein content with Pierce™ BCA Protein Assay Kit (Thermo Scientific, Cat. No. 23225) according to the manufacturer's instructions.

The result is shown in Table 4 below. It can be seen from Table 4 that the protein contents of the six postbiotic extracts of the present disclosure were significantly higher than those of the six postbiotic extracts of the prior art.

TABLE 4

| | Protein content | |
|---|---|---|
| Strain | The postbiotic extract of the present disclosure | The postbiotic extract of the prior art |
| *Lactobacillus plantarum* CB102 | 0.39% | 0.20% |
| *Lactobacillus acidophilus* JCM1132 | 0.41% | 0.21% |
| *Lactobacillus casei* JCM1134 | 0.40% | 0.20% |
| *Bifidobacterium bifidum* JCM1255 | 1.40% | 0.69% |
| *Bifidobacterium lactis* JCM10602 | 1.38% | 0.67% |
| *Bifidobacterium longum* CB108 | 1.35% | 0.70% |

C. Sodium Dodecyl Sulfate-Polyacrylamide Gel Electrophoresis (SDS-PAGE) Analysis 1 g of the respective postbiotic extract was dissolved in 20 mL of water, followed by performing SDS-PAGE analysis using an electrophoresis system (Bio-Rad).

Referring to FIG. 1, the band intensities of the six postbiotic extracts of the present disclosure were significantly higher than those of the six postbiotic extracts of the prior art. The results of this example indicate that the process of the present disclosure is effective in producing a postbiotic extract from bacterial cells, and the resultant postbiotic extract contains high levels of cell wall components (such as peptidoglycan, lipoteichoic acid, teichoic acid, glycoprotein, and proteoglycan).

Example 3. Evaluation for the Effect of Postbiotic Extract According to this Disclosure on Skin Condition A. Effect of Postbiotic Extract on TGF-β Content of Hs68 Cells Hs68 cells were divided into 25 groups, including one control group, twelve comparative groups (i.e., comparative groups L-1 to L-6 and B-1 to B-6), and twelve experimental groups (i.e., experimental groups L-1 to L-6 and B-1 to B-6). Each group of the Hs68 cells was incubated in a respective well of a 96-well culture plate containing 200 μL of DMEM at $1\times10^4$ cells/well, followed by cultivation in an incubator (37° C., 5% $CO_2$) for 24 hours. After medium change with a fresh medium, each of the cell cultures of the twelve comparative groups and twelve experimental groups was treated with the respective test postbiotic extract so that the cell culture of each group had a final concentration of the respective test postbiotic extract as shown in Table 5. The cell culture of the control group received no treatment.

TABLE 5

| Group | Test postbiotic extract | Final concentration (mg/L) |
| --- | --- | --- |
| Control group | — | 0 |
| Comparative group L-1 | The postbiotic extract of the prior art from *Lactobacillus plantarum* CB102 | 5 |
| Comparative group L-2 | | 12.5 |
| Comparative group L-3 | | 25 |
| Comparative group L-4 | | 50 |
| Comparative group L-5 | | 100 |
| Comparative group L-6 | | 200 |
| Experimental group L-1 | The postbiotic extract of the present disclosure from *Lactobacillus plantarum* CB102 | 5 |
| Experimental group L-2 | | 12.5 |
| Experimental group L-3 | | 25 |
| Experimental group L-4 | | 50 |
| Experimental group L-5 | | 100 |
| Experimental group L-6 | | 200 |
| Comparative group B-1 | The postbiotic extract of the prior art from *Bifidobacterium longum* CB108 | 5 |
| Comparative group B-2 | | 12.5 |
| Comparative group B-3 | | 25 |
| Comparative group B-4 | | 50 |
| Comparative group B-5 | | 100 |
| Comparative group B-6 | | 200 |
| Experimental group B-1 | The postbiotic extract of the present disclosure from *Bifidobacterium longum* CB108 | 5 |
| Experimental group B-2 | | 12.5 |
| Experimental group B-3 | | 25 |
| Experimental group B-4 | | 50 |
| Experimental group B-5 | | 100 |
| Experimental group B-6 | | 200 |

After cultivation in an incubator (37° C., 5% $CO_2$) for 24 hours, the respective resultant cell culture was subjected to the determination of TGF-β content according to the method described in section 1 of "General Procedures".

As shown in Table 6 below, the TGF-β contents determined in the experimental groups L-1 to L-6 were respectively higher than those determined in the comparative groups L-1 to L-6, and the TGF-β contents determined in the experimental groups B-1 to B-6 were also respectively higher than those determined in the comparative groups B-1 to B-6. This result suggests that the postbiotic extract of the present disclosure is effective in inducing TGF-β secretion in Hs68 cells.

TABLE 6

| Group | TGF-β content (pg/mL) |
| --- | --- |
| Control group | 10.5 |
| Comparative group L-1 | 10.4 |
| Comparative group L-2 | 21.6 |
| Comparative group L-3 | 42.6 |
| Comparative group L-4 | 76.4 |
| Comparative group L-5 | 88.5 |
| Comparative group L-6 | 88.7 |
| Experimental group L-1 | 20.8 |
| Experimental group L-2 | 40.9 |
| Experimental group L-3 | 73.5 |
| Experimental group L-4 | 123.1 |
| Experimental group L-5 | 154.5 |
| Experimental group L-6 | 156.7 |
| Comparative group B-1 | 12.1 |
| Comparative group B-2 | 28.2 |
| Comparative group B-3 | 67.4 |
| Comparative group B-4 | 79.1 |
| Comparative group B-5 | 86.8 |
| Comparative group B-6 | 97.6 |
| Experimental group B-1 | 20.7 |
| Experimental group B-2 | 43.7 |
| Experimental group B-3 | 98.2 |
| Experimental group B-4 | 156.3 |
| Experimental group B-5 | 199.9 |
| Experimental group B-6 | 200.3 |

B. Effect of the Combination of Postbiotic Extract with Nutritional Component on TGF-β Content of Hs68 Cells Hs68 cells were divided into 28 groups, including fourteen comparative groups (i.e., comparative groups 1 L to 7 L and 1H to 7H) and fourteen experimental groups (i.e., experimental groups 1 L to 7 L and 1B to 7B). Each group of the Hs68 cells was incubated in a respective well of a 96-well culture plate containing 200 μL of DMEM at $1\times10^4$ cells/well, followed by cultivation in an incubator (37° C., 5% $CO_2$) for 24 hours. After medium change with a fresh medium, the culture of each group was treated with a nutritional component only or additionally with the postbiotic extract of the present disclosure so that the cell culture of each group had a corresponding final concentration(s) of the nutritional component only or additionally with the postbiotic extract as shown in Table 7.

TABLE 7

| Group | Nutritional component (mg/L) | | The postbiotic extract of the present disclosure from *Lactobacillus plantarum* CB102 (mg/L) | The postbiotic extract of the present disclosure from *Bifidobacterium longum* CB108 (mg/L) |
| --- | --- | --- | --- | --- |
| Comparative group 1L | Sodium hyaluronate | 100 | — | — |
| Comparative group 1H | | 200 | — | — |
| Experimental group 1L | | 100 | 100 | — |

TABLE 7-continued

| Group | Nutritional component (mg/L) | | The postbiotic extract of the present disclosure from *Lactobacillus plantarum* CB102 (mg/L) | The postbiotic extract of the present disclosure from *Bifidobacterium longum* CB108 (mg/L) |
|---|---|---|---|---|
| Experimental group 1B | | 100 | — | 100 |
| Comparative group 2L | Vitamin C | 100 | — | — |
| Comparative group 2H | | 200 | — | — |
| Experimental group 2L | | 100 | 100 | — |
| Experimental group 2B | | 100 | — | 100 |
| Comparative group 3L | Glucosamine | 100 | — | — |
| Comparative group 3H | | 200 | — | — |
| Experimental group 3L | | 100 | 100 | — |
| Experimental group 3B | | 100 | — | 100 |
| Comparative group 4L | Chondroitin | 100 | — | — |
| Comparative group 4H | | 200 | — | — |
| Experimental group 4L | | 100 | 100 | — |
| Experimental group 4B | | 100 | — | 100 |
| Comparative group 5L | Type II collagen | 100 | — | — |
| Comparative group 5H | | 200 | — | — |
| Experimental group 5L | | 100 | 100 | — |
| Experimental group 5B | | 100 | — | 100 |
| Comparative group 6L | Fish skin and scale collagen peptide | 100 | — | — |
| Comparative group 6H | | 200 | — | — |
| Experimental group 6L | | 100 | 100 | — |
| Experimental group 6B | | 100 | — | 100 |
| Comparative group 7L | Undenatured type II collagen | 100 | — | — |
| Comparative group 7H | | 200 | — | — |
| Experimental group 7L | | 100 | 100 | — |
| Experimental group 7B | | 100 | — | 100 |

After cultivation in an incubator (37° C., 5% $CO_2$) for 24 hours, the respective resultant cell culture was subjected to the determination of TGF-β content according to the method described in section 1 of "General Procedures".

As shown in Table 8 below, when sodium hyaluronate was used as a nutritional supplement, the TGF-β contents determined in the experimental groups 1 L and 1B were higher than those determined in the comparative groups 1 L and 1H. Besides, when the other six nutritional supplements were used, similar satisfactory results were observed with respect to the experimental groups 2 L to 7 L and 2B to 7B, indicating that the combination of a postbiotic extract with nutritional supplements is effective in inducing TGF-β secretion in Hs68 cells.

TABLE 8

| Group | TGF-β content (pg/mL) |
|---|---|
| Comparative group 1L | 289.9 |
| Comparative group 1H | 304.8 |
| Experimental group 1L | 397.7 |
| Experimental group 1B | 424.1 |
| Comparative group 2L | 52.2 |
| Comparative group 2H | 63.1 |
| Experimental group 2L | 154.7 |
| Experimental group 2B | 181.1 |
| Comparative group 3L | 51.1 |
| Comparative group 3H | 61.3 |
| Experimental group 3L | 154.1 |
| Experimental group 3B | 180.5 |
| Comparative group 4L | 120.5 |
| Comparative group 4H | 128.8 |
| Experimental group 4L | 224.0 |
| Experimental group 4B | 250.4 |
| Comparative group 5L | 178.8 |
| Comparative group 5H | 188.7 |
| Experimental group 5L | 284.2 |
| Experimental group 5B | 310.6 |
| Comparative group 6L | 51.5 |
| Comparative group 6H | 61.5 |
| Experimental group 6L | 155.3 |
| Experimental group 6B | 181.7 |
| Comparative group 7L | 52.1 |
| Comparative group 7H | 60.6 |
| Experimental group 7L | 154.7 |
| Experimental group 7B | 181.1 |

C. Effect of Postbiotic Extract on Proliferation of Hs68 Cells

Hs68 cells were divided into 3 groups, including one control group and two experimental groups (i.e., experimental groups L and B). Each group of the Hs68 cells was incubated in a respective well of a 96-well culture plate containing 200 μL of DMEM at $1 \times 10^4$ cells/well, followed by cultivation in an incubator (37° C., 5% $CO_2$) for 24 hours. After medium change with a fresh medium, each of the cell cultures of the two experimental groups was treated with the respective test postbiotic extract so that the cell culture of each group had a final concentration of the respective test postbiotic extract as shown in Table 9. The cell culture of the control group received no treatment.

TABLE 9

| Group | Test postbiotic extract | Final concentration (mg/L) |
|---|---|---|
| Control group | — | 0 |
| Experimental group L | The postbiotic extract of the present disclosure from *Lactobacillus plantarum* CB102 | 100 |
| Experimental group B | The postbiotic extract of the present disclosure from *Bifidobacterium longum* CB108 | 100 |

After cultivation in an incubator (37° C., 5% $CO_2$) for 24 hours, the respective resultant cell culture was stained with 3-(4,5-Dimethylthiazol-2-yl)-2,5-diphenyltetrazolium bromide (MTT), followed by subjecting the stained cells to determination of absorbance at a wavelength of 570 nm by a spectrophotometer. The $OD_{570}$ values obtained were subsequently converted to cell numbers based on a correlation curve previously prepared by plotting different known cell numbers of Hs68 cells versus their $OD_{570}$ values.

As shown in Table 10 below, the cell numbers determined in the experimental groups L and B were each higher than that determined in the control group, indicating that the postbiotic extract of the present disclosure is capable of improving Hs68 cell proliferation.

TABLE 10

| Group | Cell number |
|---|---|
| Control group | $1.1 \times 10^4$ |
| Experimental group L | $1.7 \times 10^4$ |
| Experimental group B | $2.1 \times 10^4$ |

D. Effect of the Combination of Postbiotic Extract with Nutritional Component on Proliferation of Hs68 Cells Hs68 cells were divided into 28 groups, including fourteen comparative groups (i.e., comparative groups 1 L to 7 L and 1H to 7H) and fourteen experimental groups (i.e., experimental groups 1 L to 7 L and 1B to 7B). Each group of the Hs68 cells was incubated in a respective well of a 96-well culture plate containing 200 μL of DMEM at $1 \times 10^4$ cells/well, followed by cultivation in an incubator (37° C., 5% $CO_2$) for 24 hours. After medium change with a fresh medium, the culture of each group was treated with a nutritional component only or additionally with the postbiotic extract of the present disclosure so that the cell culture of each group had a corresponding final concentration(s) of the nutritional component only or additionally with the postbiotic extract as shown in Table 7 above.

After cultivation in an incubator (37° C., 5% $CO_2$) for 24 hours, the cell number of each group was determined according to the method described in section C of this example. The fold increase of viable cells was calculated using the following Equation (II):

$$C = D/E \tag{II}$$

where C=fold increase of viable cells
D=cell number of respective experimental group or comparative group
E=cell number of corresponding comparative group 1 L, 2 L, 3 L, 4 L, 5 L, 6 L, or 7 L As shown in Table 11 below, when sodium hyaluronate was used as a nutritional supplement, the fold increases of viable cells determined in the experimental groups 1 L and 1B were higher than those determined in the comparative groups 1 L and 1H. Besides, when the other six nutritional supplements were used, similar satisfactory results were observed with respect to the experimental groups 2 L to 7 L and 2B to 7B, indicating that the combination of a postbiotic extract with nutritional supplements is capable of improving the proliferation of Hs68 cells.

TABLE 11

| Group | Fold increase of viable Cells |
|---|---|
| Comparative group 1L | 1.0 |
| Comparative group 1H | 1.1 |
| Experimental group 1L | 1.3 |
| Experimental group 1B | 1.3 |
| Comparative group 2L | 1.0 |
| Comparative group 2H | 1.1 |
| Experimental group 2L | 1.5 |
| Experimental group 2B | 1.5 |
| Comparative group 3L | 1.0 |
| Comparative group 3H | 1.1 |
| Experimental group 3L | 1.2 |
| Experimental group 3B | 1.2 |
| Comparative group 4L | 1.0 |
| Comparative group 4H | 1.1 |
| Experimental group 4L | 1.3 |
| Experimental group 4B | 1.3 |
| Comparative group 5L | 1.0 |
| Comparative group 5H | 1.1 |
| Experimental group 5L | 1.2 |
| Experimental group 5B | 1.2 |
| Comparative group 6L | 1.0 |
| Comparative group 6H | 1.1 |
| Experimental group 6L | 1.4 |
| Experimental group 6B | 1.4 |
| Comparative group 7L | 1.0 |
| Comparative group 7H | 1.1 |
| Experimental group 7L | 1.4 |
| Experimental group 7B | 1.4 |

Summarizing the above test results, it is clear that the postbiotic extract of the present disclosure is effective in inducing TGF-β secretion in skin cells and improving proliferation of skin cells, and hence can promote skin regeneration, enhance skin quality or appearance, and prevent skin aging.

All patents and references cited in this specification are incorporated herein in their entirety as reference. Where there is conflict, the descriptions in this case, including the definitions, shall prevail.

While the disclosure has been described in connection with what are considered the exemplary embodiments, it is understood that this disclosure is not limited to the disclosed embodiments but is intended to cover various arrangements included within the spirit and scope of the broadest interpretation so as to encompass all such modifications and equivalent arrangements.

What is claimed is:

1. A method for of improving skin condition, comprising administering to a subject in need thereof a postbiotic extract, wherein the postbiotic extract is prepared by a process including the steps of:
    a) providing a whey protein having an isoelectric point of 4.4, and a dextrin having an isoelectric point of 5.2;
    b) admixing the whey protein and a probiotic bacterium with water having a pH value of 7.5, so as to form a mixture, wherein the probiotic bacterium is selected from the group consisting of *Lactobacillus plantarum* CB102, *Lactobacillus acidophilus* JCM1132, *Lactobacillus casei* JCM1134, *Bifidobacterium bifidum* JCM1255, *Bifidobacterium lactis* JCM10602, *Bifidobacterium longum* CB108, and combinations thereof;
    c) adding the dextrin into the mixture, followed by adjusting the pH value of the dextrin-added mixture to between 4.4 and 5.2, so that a precipitate is formed; and
    d) subjecting the precipitate to an acid hydrolysis treatment with lactic acid to isolate the cell wall of the probiotic bacterium, so as to obtain the postbiotic extract.

2. The method according to claim 1, wherein the skin condition to be improved is selected from the group consisting of skin regeneration, skin elasticity, skin wrinkles, skin aging, wound healing, and combinations thereof.

* * * * *